United States Patent
Piccolo et al.

(10) Patent No.: US 7,087,548 B2
(45) Date of Patent: Aug. 8, 2006

(54) PREPARATION AND USE OF A HETEROGENEOUS RHODIUM CATALYST FOR THE HYDROGENATION OF A DOUBLE BOND OF AN α-β-UNSATURATED CARBONYL COMPOUND

(75) Inventors: Oreste Piccolo, Sirtori (IT); Alessandra Verrazzani, Pisa (IT)

(73) Assignee: Chemi Spa, Milan (IT)

( * ) Notice: Subject to any disclaimer, the term of this patent is extended or adjusted under 35 U.S.C. 154(b) by 0 days.

(21) Appl. No.: 10/493,745

(22) PCT Filed: Oct. 24, 2002

(86) PCT No.: PCT/EP02/11885

§ 371 (c)(1),
(2), (4) Date: Apr. 22, 2004

(87) PCT Pub. No.: WO03/037508

PCT Pub. Date: May 8, 2003

(65) Prior Publication Data

US 2005/0033092 A1 Feb. 10, 2005

(30) Foreign Application Priority Data

Oct. 29, 2001 (IT) .......................... MI2001A2267

(51) Int. Cl.
*B01J 31/00* (2006.01)
(52) U.S. Cl. ...................... 502/150; 502/155; 568/434
(58) Field of Classification Search ................ 502/150, 502/155; 568/434
See application file for complete search history.

(56) References Cited

U.S. PATENT DOCUMENTS

| | | | | |
|---|---|---|---|---|
| 4,292,452 A * | 9/1981 | Lee et al. | ..................... | 568/881 |
| 4,415,478 A * | 11/1983 | Suggitt et al. | ............... | 502/181 |
| 4,950,798 A * | 8/1990 | Stobart et al. | ............... | 568/454 |
| 5,175,311 A * | 12/1992 | Doyle | ........................ | 549/302 |
| 5,296,595 A * | 3/1994 | Doyle | ........................ | 540/200 |
| 5,814,709 A * | 9/1998 | De Boer et al. | ............. | 525/337 |
| 6,025,295 A * | 2/2000 | Tanielyan et al. | ............ | 502/154 |
| 6,025,502 A * | 2/2000 | Winklter et al. | .............. | 549/21 |
| 6,150,564 A * | 11/2000 | Brocker et al. | .............. | 568/462 |
| 6,232,506 B1 * | 5/2001 | Kido et al. | .................. | 568/390 |
| 6,410,746 B1 * | 6/2002 | Davies | ........................ | 548/403 |
| 6,420,304 B1 * | 7/2002 | Tsai et al. | .................... | 502/207 |
| 6,472,565 B1 * | 10/2002 | Bahrmann et al. | ........... | 568/454 |
| 6,544,923 B1 * | 4/2003 | Ying et al. | ................... | 502/159 |
| 6,800,720 B1 * | 10/2004 | Yamamoto et al. | ......... | 528/403 |
| 6,815,509 B1 * | 11/2004 | Miyamoto et al. | .......... | 525/338 |

FOREIGN PATENT DOCUMENTS

GB 916119 A1 1/1963

OTHER PUBLICATIONS

Venkatraman, S., et al., "Quasi-nature catalysis: conjugated addition of alpha, beta-unsaturated carbonyl compounds with aryl and vinyltin reagents catalyzed by rhodium in air and water" Tetrahedron Lett. 42:4459-4462, Pergamon Press (2001).*

Sato et al., "Rhodium-catalyzed isomerication of 1,3-diene monoepoxides to alpha., .beta-unsaturated carbonyl compounds," Journal of Organometallic Chemistry, vol. 359, pp. 255-266 (1989).*

Philippe Drognat Landre et al., "Colloidal Rhodium: A New Catalytic System for the Reduction of Dibenzo-18-crown-6 Ether", Journal of Catalysis 147 (1994) 214-222.

H. Bönnemann, et al., "Nanoscale Colloidal Metals and Alloys Stabilized by Solvents and Surfactants Preparation and Use of Catalyst Precursors 1,2", Journal of Organometallic Chemistry 520 (1996) 143-163.

Jaques Azran et al., "Selective Hydrogenation of alpha, beta-Unsaturated Carbonyl Compounds by Rhodium Trichloride and Aliquat-336 in a Two-Phase Liquid System", Journal of Molecular Catalysis, 34 (1986) 229-234.

Masahiko Yamaguchi et al., "Stereoselective Hydrogenation of Tetrasubstituted Enones", SYNLETT, Jan. 1997, pp. 117-118.

(Continued)

*Primary Examiner*—J. A. Lorengo
*Assistant Examiner*—Jennine Brown
(74) *Attorney, Agent, or Firm*—Darby & Darby

(57) ABSTRACT

A process for preparing an Rh-based catalytic system heterogenized on an organic or mineral support, characterized in that: a) a rhodium derivative with a valency state>0 is reduced in an ether or aromatic solvent and in the presence of a compound chosen from the group consisting of lipophilic tertiary amines, lipophilic tertiary amides and lipophilic quaternary ammonium salts, and b) the mixture thus obtained is adsorbed onto a suitable organic or mineral support. Use of the abovementioned catalytic system to hydrogenate a C=C double bond of an α,β-unsaturated carbonyl compound.

26 Claims, No Drawings

OTHER PUBLICATIONS

J.A. Cabello et al., "Chemoselective Hydrogeneration of alpha, beta-Unsaturated Carbonyl Compounds on AlPO Supported Rh Catalysts", React. Kinet. Catal. Lett., vol. 28, 1984, pp. 447-451.

International Search Report issued on PCT/EP02/11885 of which present application is the U.S. National Stage Application.

* cited by examiner

PREPARATION AND USE OF A HETEROGENEOUS RHODIUM CATALYST FOR THE HYDROGENATION OF A DOUBLE BOND OF AN α-β-UNSATURATED CARBONYL COMPOUND

The present invention relates to the preparation and use of an Rh-based heterogeneous catalyst with high catalytic activity, good stability and high selectivity for the hydrogenation of a C=C double bond of an α,β-unsaturated carbonyl compound.

In particular, the present invention relates to the hydrogenation of a compound of general formula (I) to give a compound of general formula (II):

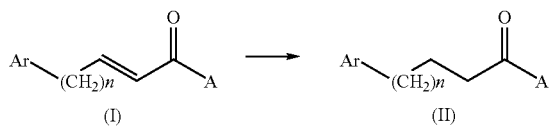

in which Ar, A and n have the meanings given below.

The hydrogenation of multifunctional compounds such as, for example, α,β-unsaturated carbonyl compounds also containing an aromatic or heteroaromatic ring has been and continues to be the subject of both academic and applied research, with the aim of identifying catalysts that are highly selective towards a single function, such as, for example, the C=C double bond, with formation of small amounts of by-products such as saturated and/or unsaturated alcohols and/or by-products resulting from the partial or total hydrogenation of the aromatic or heteroaromatic nucleus.

In the course of the present description, the expression "small amounts" means an amount ≦2% or, even more preferably, ≦1%.

Specifically, when larger amounts of by-products are formed, it is usually difficult or even impossible to purify the desired final compounds without being penalized by significant losses of yield during the purification treatment. This is especially the case when products for pharmaceutical use are concerned, i.e. which have relatively high purity requirements (>99.5%).

Patent GB-A-916 119 describes a process for hydrogenating the olefinic double bond of α,β-unsaturated aldehydes and ketones. Although cinnamaldehyde and benzalacetophenone are mentioned among the hydrogenatable products, the examples refer only to carbonyl compounds lacking an aromatic substituent. According to these examples, the reaction is preferably carried out in the absence of solvent or in the presence of polar solvents, at atmospheric pressure and at a temperature of 25° C. Although other heterogeneous rhodium catalysts are envisaged, a commercial catalyst is used, 5% Rh/C.

However, the present inventors have found that by working under the conditions described in GB-A-916 119, either in alcoholic solvents or in toluene, with commercial catalysts such as 5% Rh/C and 5% Rh/Al$_2$O$_3$, the substrate (I) in which Ar is (6'-methoxy-2'-naphthyl), n=0 and A=methyl shows moderately good selectivity (worse when the solvent is polar), but a mediocre conversion (≦50%) even after long reaction times. The present inventors have moreover found that more advantageous results are obtained by working at relatively higher temperatures and pressures. However, even under these conditions, the production efficiency is still entirely insufficient.

The reduction of compound (I), in which Ar=phenyl, n=0 and A=H, alkyl or phenyl, has also been described in React. Kinet. Catal. Lett. 26, 447 (1984). The said document describes a hydrogenation in methanol, at room temperature and low pressure, with a non-commercial 1% Rh/AlPO$_4$ catalyst and with a substrate/Rh ratio (w/w) of between 300 and 500. When A=H, no reduction takes place. In the other cases, the reduction is fast, although it is sensitive to the steric hindrance. The authors state, without, however, providing experimental data, that the selectivity is quite high and that no saturated or unsaturated alcohols are formed. It should be noted, however, that the hydrogenation products thus obtained need to be purified by crystallization or chromatography on silica. In addition, the preparation of the abovementioned catalyst is too complicated to be used in an industrial production. Specifically, it involves the preparation of the AlPO$_4$ support, its impregnation with an aqueous rhodium trichloride solution, drying the precatalytic system thus obtained at 120° C. and reducing the said precatalytic system under a flow of hydrogen at 200° C.

In more recent documents [Synlett, 117 (1997) and J. Mol. Catalysis A, 154, 237 (2000)] for the hydrogenation of hindered carbonyl compounds, with tri- or tetrasubstituted C=C double bonds, 5% Rh on charcoal or alumina with a substrate/Rh ratio (w/w)=20 and 10% Pd on charcoal (pyridine co-catalyst) in a substrate/Pd ratio (w/w)=100 are used as preferred catalysts. The reaction is carried out in an aromatic solvent since it is stated to be more selective than the polar solvents previously used, even though the reaction rate may be relatively lower. In the second of the two documents the effect on the selectivity of various parameters such as the nature of the support, the presence of additives, the structure of the substrate to be hydrogenated, etc. are also pointed out.

Thus, the prior art teaches that selective hydrogenation with heterogeneous catalysts requires the study and refinement of many parameters and that this frequently relates to the development of a specific catalyst for each substrate to be hydrogenated.

Normally, the higher the required selectivity, the lower the catalytic activity of the commercially available catalysts. Thus, their production efficiency is often too low for them to be used on an industrial scale. Since these catalysts also consist of particles of relatively expensive, and also toxic, precious metals distributed over the surface of an inert support, parameters that are important for their industrial application also include a) a distribution that is as homogeneous as possible of the metal particles; b) good stability, with little or no release of the metal (to furthermore avoid contamination of the hydrogenation product); c) a substrate/metal ratio (w/w) that is as favourable as possible; d) the possibility of multiple recycling without any loss of catalytic activity or selectivity; e) little or no sensitivity to the impurities that may be present in the intermediate (I) subjected to hydrogenation, or to other reaction parameters such as, for example, the dryness of the solvent.

In the course of the present description, the expression "production efficiency (TOF)" means the ratio: moles of substrate/gram-atoms of metal/time, where the time is expressed in hours.

It has also been reported that a number of rhodium-based catalysts may be used under two-phase or microemulsion conditions. However, these conditions have not been used on an industrial scale.

J. Mol. Catalysis 34, 229 (1986) described the hydrogenation of a number of α,β-unsaturated carbonyl compounds (I) in which Ar=phenyl or phenyl substituted with a chlorine atom or a methyl group, n=0 and A=phenyl or COOC$_2$H$_5$, in the presence of RhCl$_3$/Aliqua™ 336, in a 1/(1–1.8) ratio, in a water/dichloroethane two-phase system at 30° C. and at atmospheric pressure. For this catalytic system which, after treatment with hydrogen and interaction with the substrate, conserves an Rh—Cl bond, the presence of water is essential. In addition, this catalytic system has relatively low catalytic activity and production efficiency, is relatively inefficient in aromatic solvents and is extremely sensitive to the steric effects of the substrate to be hydrogenated. To overcome the low production efficiency, recycling of said catalyst was envisaged, but no data regarding the kinetics and selectivity of the recycled catalyst were given. Finally, it should be pointed out that the same authors [J. Mol. Catalysis 34, 221 (1986)] have demonstrated that the same catalytic system, still under mild conditions, is suitable for hydrogenating naphthalene derivatives to give tetralin. Therefore, this system cannot be used to selectively hydrogenate a C=C double bond of an α,β-unsaturated carbonyl compound containing a naphthalene ring.

In more recent studies, such as J. Mol. Catalysis 87, 107 (1994) and J. Catalysis 147, 214 (1994), the reduction of disubstituted aromatic rings or, respectively, of dibenzo-18-crown-6 ethers, is carried out at atmospheric pressure and at room temperature in the presence of two-phase catalytic systems based on RhCl$_3$/trioctylamine or tricaprylmethylammonium, thus confirming that these catalytic systems are particularly suitable for hydrogenating aromatic substrates and that, therefore, they cannot be used to selectively hydrogenate a C=C double bond of an α,β-unsaturated carbonyl compound containing an aromatic ring.

In addition to the drawbacks already mentioned, the abovementioned systems also have the following drawbacks: (a) in order to avoid the presence of metallic contaminants in the final hydrogenated product, it is necessary to make the colloidal catalytic particles heterogeneous; (b) in order to be able to reuse the catalytic system several times, it is necessary to select a suitable support that does not release the metal. However, the pursuit of these objectives is obstructed by the fact that there is relatively little information regarding the techniques for immobilizing colloidal metal particles; this is especially true as regards reproducible techniques. Thus, there is a need for a fundamental condition for the development and use of heterogeneous catalysts at the industrial level.

Chemistry Letters 149 (1987) describes the hydrogenation, at atmospheric pressure and room temperature, of olefinic systems in a 1/1 water/ethanol mixture in the presence of a catalyst consisting of a dispersion of rhodium colloidal particles protected with a copolymer of methacrylate and N-vinyl-2-pyrrolidone on a polyacrylamide gel containing amine groups. However, this solvent mixture is unsuitable in the case of lipophilic organic compounds, since these compounds are relatively insoluble in the said mixture.

Surprisingly, a process that is simple and easy to apply on an industrial scale has now been found, for preparing an Rh-based catalytic system heterogenized on an organic or mineral support, which has high catalytic activity (substrate/Rh w/w ratio up to values of an order of magnitude of 10$^4$) and at the same time high selectivity with regard to the reduction of substrates of general formula (I) to give, in high yield, high chemical purity and high production efficiency, the corresponding derivatives of general formula (II).

Thus, a first subject of the present invention is a process for preparing an Rh-based catalytic system heterogenized on an organic or mineral support, characterized in that:

a) a rhodium derivative with a valency state>0 is reduced in an ether or aromatic solvent and in the presence of a compound chosen from the group consisting of lipophilic tertiary amines, lipophilic tertiary amides and lipophilic quaternary ammonium salts, and b) the mixture thus obtained is adsorbed onto a suitable organic or mineral support.

Preferably, the abovementioned reduction is carried out with hydrogen or by hydrogen transfer from a suitable hydrogen donor such as, for example, formic acid and ammonium or alkylammonium salts thereof in which the alkyl contains from 1 to 20 carbon atoms.

Advantageously, the said reduction is performed under mild conditions. The pressure is preferably 5 atm (73.45 psi) or less. The temperature is preferably between 15 and 40° C. Higher pressures and temperatures do not afford any particular advantages.

Preferably, the rhodium derivative with a valency state>0 is a halide.

Typical examples of ether solvents are tetrahydrofuran, 1,2-dimethoxyethane, diglyme (CH$_3$O—CH$_2$—CH$_2$—O—CH$_2$—CH$_2$—OCH$_3$) and the like.

Typical examples of aromatic solvents are toluene, mesitylene, isopropylbenzene, cumene and the like.

Preferably, the lipophilic tertiary amine is an amine of formula NTT'T", in which T, T' and T", which may be identical or different, are a linear or branched alkyl containing from 4 to 20 carbon atoms, a cycloalkyl containing from 5 to 10 carbon atoms or an alkylphenyl in which the alkyl contains from 1 to 20 carbon atoms.

In turn, the lipophilic tertiary amide is preferably an amide X—CO—NX'X", in which X' and X", which may be identical or different, are a linear or branched alkyl containing from 4 to 20 carbon atoms, a cycloalkyl containing from 5 to 10 carbon atoms or an alkylphenyl in which the alkyl contains from 1 to 20 carbon atoms. The nature of X is not crucial, and may be any group of aliphatic or aromatic nature. Typical examples of X are methyl, hexyl, lauryl, stearyl, phenyl and naphthyl.

Finally, the lipophilic quaternary ammonium salt is a quaternary salt of formula [NY$^1$Y$^2$Y$^3$Y$^4$]$^+$ Z$^-$ in which Y$^1$, Y$^2$, Y$^3$ and Y$^4$, which may be identical or different, are a linear or branched alkyl containing from 1 to 20 carbon atoms, a cycloalkyl containing from 5 to 10 carbon atoms or an alkylphenyl in which the alkyl contains from 1 to 20 carbon atoms, on condition that the total number of carbon atoms in the quaternary salt is at least 14; Z$^-$ is Br$^-$, Cl$^-$, OH$^-$ or HSO$_4^-$.

Advantageously, the tertiary amine is trioctylamine (TOA) or ammonium salt) and a support, in the chosen solvent.

The heterogeneous catalysts according to the present invention allow the production of compounds of general formula (II) with a selectivity ≧98%, a production efficiency (TOF) at least up to 3×10$^3$ h$^{-1}$ and a use (w/w) of substrate/Rh of up to 10$^4$.

Thus, a second subject of the present invention is a process for hydrogenating the C=C double bond in α,β-unsaturated carbonyl compounds of general formula (I) according to the following reaction scheme:

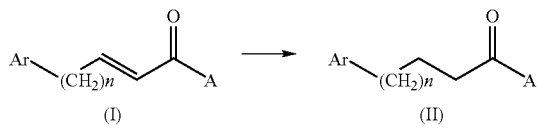

in which

A is hydrogen, linear or branched alkyl containing from 1 to 8 carbon atoms, cycloalkyl containing from 5 to 10 carbon atoms, COOR or CONRR' in which R and R', which may be identical or different, are hydrogen, linear or branched alkyl containing from 1 to 8 carbon atoms or cycloalkyl containing from 5 to 10 carbon atoms, or A has the meanings given below for Ar;

n is 0, 1 or 2;

Ar is phenyl, naphthyl or a 5- to 7-membered heteroaryl containing 1 or 2 hetero atoms chosen from O, N and S, in which the said phenyl, naphthyl and heteroaryl may be substituted with one or more $C_1$–$C_8$ alkyl groups or one or more OH, OR, halogen, COOR or CONRR' groups, in which R and R', which may be identical or different, are hydrogen, benzyl, linear or branched alkyl containing from 1 to 8 carbon atoms or cycloalxyl containing from 5 to 10 carbon atoms, characterized in that the said hydrogenation is carried out in the presence of an Rh-based catalytic system heterogenized on an organic or mineral support, obtained by (i) reducing a rhodium derivative with a valency state>0 in an ether or aromatic solvent and in the presence of a compound chosen from the group consisting of lipophilic tertiary amines, lipophilic tertiary amides and lipophilic quaternary ammonium salts, and (ii) adsorbing the mixture thus obtained onto a suitable organic or mineral support.

Reference is made to the above description as regards the preparation of the abovementioned catalyst.

Preferably, the said hydrogenation of the C=C double bond of the α,β-unsaturated carbonyl compounds of general formula (I) is carried out at a temperature of between 0° and 100° C. and even more preferably between 20° and 80° C.

In turn, the pressure is preferably between 1 (14.69 psi) and 20 atm (293.8 psi).

Advantageously, the said hydrogenation is carried out in the presence of a solvent of medium or low polarity such as, for example, a linear or branched aliphatic hydrocarbon containing from 6 to 12 carbon atoms; a cyclic hydrocarbon containing from 6 to 10 carbon atoms; an aromatic hydrocarbon such as, for example, toluene, xylene, mesitylene, isopropylbenzene or cumene; an aliphatic ester such as, for example, ethyl acetate, isopropyl acetate or butyl acetate; an aliphatic ether such as, for example, tetrahydrofuran; or a chlorinated aliphatic solvent such as, for example, methylene chloride.

The hydrogenation process according to the present invention was found to be particularly efficient with regard to the hydrogenation of the C=C double bond of the α,β-unsaturated carbonyl compound of general formula (I) in which Ar is (6'-methoxy-2'-naphthyl), n=0 and A=methyl, to give 4-(6'-methoxy-2'-naphthyl)-2-butanone (Nabumetone™), which is an important medicinal product.

A typical example of another α,β-unsaturated carbonyl compound of general formula (I) in which the C=C double bond is selectively hydrogenated according to the present invention is that in which Ar is (2',3'-dimethoxyphenyl), n=0 and A is COOH, COO($C_1$–$C_4$)alkyl or COO-benzyl.

The following non-limiting examples serve to illustrate the present invention.

EXAMPLE 1

Preparation of Rh(TOA)/$Al_2O_3$ 42 g of γ-alumina, 200 mg of $RhCl_3$ · $xH_2O$ (43.5% Rh), 140 ml of THF and 1.44 ml of trioctylamine (TOA) were loaded, in the above order, at 25° C., into a 0.6 l glass reactor equipped with a mechanical stirrer, a thermometer and a manometer.

The mixture was placed under stirring. 3 cycles of argon-vacuum and 2 cycles of $H_2$-vacuum were performed. Next, the mixture was placed under pressure with hydrogen up to 0.5 atm (7.35 psi). After stirring for 24 hours under $H_2$, the reaction was stopped.

The atmosphere was made inert by performing three cycles of Ar-vacuum. The reaction mixture was then filtered on a Buchner funnel.

The solid was washed with 140 ml of THF and then with 140 ml of $H_2O$. Finally, the solid was pressed and unloaded.

55 g (K.F. 29.6%) of Rh(TOA)/$Al_2O_3$ with a rhodium content equal to 0.12% were thus obtained.

EXAMPLE 2

Preparation of Rh(TOA)/$Al_2O_3$ 105 g of γ-alumina, 500 mg of $RhCl_3$ · $xH_2O$ (43.5% Rh), 350 ml of THF and 3.6 ml of TOA were loaded, in the above order, at 25° C., into a 1 l glass reactor equipped with a mechanical stirrer, a thermometer and a manometer.

The mixture was placed under stirring. 3 cycles of argon-vacuum and 2 cycles of $H_2$-vacuum were performed. The mixture was then placed under pressure with hydrogen up to 0.5 atm (7.35 psi). After stirring for 24 hours under $H_2$, the reaction was stopped.

The atmosphere was made inert by performing three cycles of Ar-vacuum. The reaction mixture was then filtered through a Buchner funnel.

The solid was washed with 100 ml of THF and then with 100 ml of $H_2O$. Finally, the solid was dried under reduced pressure.

100 g (K.F. ca. 3%) of Rh(TOA)/$Al_2O_3$ with a rhodium content equal to 0.16% were thus obtained.

EXAMPLE 3

Preparation of Rh(TOA)/$Al_2O_3$ 42 kg of γ-alumina, 0.2 kg of $RhCl_3$ · $xH_2O$ (43.5% Rh), 124 kg of THF and 1.17 kg of TOA were loaded, in the above order, at 25° C., into a 200 l Hastelloy reactor.

The mixture was placed under stirring. 3 cycles of nitrogen-vacuum and 2 cycles of $H_2$-vacuum were performed. The mixture was then placed under pressure with hydrogen up to 0.5 atm (7.35 psi). After stirring at 25–30° C. for 24 hours under $H_2$, the reaction was stopped.

The atmosphere was made inert by performing three cycles of nitrogen-vacuum. The reaction mixture was then filtered through a Buchner funnel.

The solid was washed with 2×62 kg of THF, 3×40 l of $H_2O$ and then dried for 1 hour under reduced pressure (50 mmHg) at 50° C.

40 kg (K.F. 3.3%) of Rh(TOA)/Al$_2$O$_3$ with a rhodium content equal to 0.16% were thus obtained.

EXAMPLE 4

Preparation of Rh(TOA)/Al$_2$O$_3$ 100 mg of RhCl$_3$ · xH$_2$O (43.5% Rh), 10 ml of THF and 0.72 ml of TOA were loaded, at 25° C., into a 50 ml glass round-bottomed flask equipped with a magnetic stirrer and a thermometer.

The mixture was placed under stirring. 3 cycles of argon-vacuum and 2 cycles of H$_2$-vacuum were performed. The mixture was then placed under a hydrogen atmosphere for 24 hours.

The solution thus obtained was transferred into another round-bottomed flask containing a suspension of 20 g of γ-alumina in 35 ml of THF. The mixture was stirred for 6 hours under an H$_2$ atmosphere. The atmosphere was then made inert by means of three cycles of Ar-vacuum.

The reaction mixture was filtered through a Buchner funnel and the solid was washed with 20 ml of THF and then with 2×10 ml of hexane.

After drying under reduced pressure, 20 g of anhydrous Rh(TOA)/Al$_2$O$_3$ with a rhodium content equal to 0.15% were obtained.

EXAMPLE 5

Preparation of 4-(6'-methoxy-2'-naphthyl)-2-butanone 14.9 g of the compound of general formula (I) in which Ar=(6'-methoxy-2'-naphthyl), n=0 and A=methyl, and 1.42 g of wet catalyst, prepared according to Example 1, in 100 ml of toluene were placed in a 250 ml autoclave.

Working at 75° C. and under 5 atm (73.45 psi) of hydrogen, the conversion was complete after 2.5 hours, with a selectivity towards Nabumetone of 98.7% and a TOF of ca. $1.6 \times 10^3 \text{ h}^{-1}$.

At the end of the reaction, the mixture was filtered and the catalyst was reused in unmodified form on a fresh amount of compound (I), with identical results in terms of kinetics and selectivity.

After recycling a further 3 times, the reaction was complete after 4.5 hours with a selectivity >99% and a TOF of ca. $0.9 \times 10^3 \text{ h}^{-1}$.

EXAMPLE 6

Preparation of 4-(6'-methoxy-2'-naphthyl)-2-butanone 14.9 g of the compound of general formula (I) in which Ar=(6'-methoxy-2'-naphthyl), n=0 and A=methyl, and 0.95 g of substantially anhydrous catalyst, prepared according to Example 2, in 100 ml of toluene were placed in a 250 ml autoclave. The suspension was stirred at 50° C. and under 5 atm (73.45 psi) of hydrogen. After 3.5 hours, the conversion was complete, with a selectivity towards Nabumetone of 99% and a TOF of ca. $1.3 \times 10^3 \text{ h}^{-1}$.

EXAMPLE 7

Preparation of 4-(6'-methoxy-2'-naphthyl)-2-butanone

Working as in Example 6, but at 75° C. and under 15 atm (220.35 psi) of hydrogen, the conversion was complete after 1.5 hours, with a selectivity towards Nabumetone of 98.7% and a TOF of ca. $3 \times 10^3 \text{ h}^{-1}$.

EXAMPLE 8

Preparation of 4-(6'-methoxy-2'-naphthyl)-2-butanone 10 g of the compound of general formula (I) in which Ar=(6'-methoxy-2'-naphthyl), n=0 and A=methyl, and 1.42 g of wet catalyst, prepared according to Example 1, in 70 ml of toluene were placed in a 250 ml autoclave. The suspension was stirred at 50° C. and under 5 atm (73.45 psi) of hydrogen. After 4.5 hours, the conversion was complete, with a selectivity towards Nabumetone of 98.5% and a TOF of ca. $0.6 \times 10^3 \text{ h}^{-1}$.

EXAMPLE 9

Preparation of 4-(6'-methoxy-2'-naphthyl)-2-butanone 1.18 kg of catalyst prepared according to Example 3 and a toluene solution (130 l) containing 23.6 kg of the compound of general formula (I) in which Ar=(6'-methoxy-2'-naphthyl), n=0 and A=methyl, were loaded, in the above order, at 25° C., into a 200 l Hastelloy reactor.

The mixture was placed under stirring (200 rpm) and 3 cycles of nitrogen-vacuum and 2 cycles of H$_2$-vacuum were performed. The reaction mixture was then heated to 50° C. and placed under pressure with hydrogen up to 15 atm (220.35 psi).

After 4.5 hours, the conversion was complete, with a selectivity towards Nabumetone of 98.7% and a TOF of ca. $1.3 \times 10^3 \text{ h}^{-1}$

COMPARATIVE EXAMPLE 1

Preparation of 4-(6'-methoxy-2'-naphthyl)-2-butanone

Working as in Example 6, but using 0.075 g of a commercial anhydrous 5% Rh/Al$_2$O$_3$ catalyst or 0.15 g of a commercial 5% Rh/C catalyst with a water content of about 50% (with a precious metal content about 2–2.5 times higher than that of the present invention) and under identical temperature and pressure conditions, the conversion was <50%.

With the abovementioned commercial catalysts, the conversion was 97–98% only after 6 hours at 20 atm (293.8 psi) and 70° C. However, the selectivity was less than 98% and the TOF was less than $3 \times 10^2 \text{ h}^{-1}$.

COMPARATIVE EXAMPLE 2

Preparation of 4-(6'-methoxy-2'-naphthyl)-2-butanone 4 g of the compound of general formula (I) in which Ar=(6'-methoxy-2'-naphthyl), n=0 and A=methyl, and 0.02 g of a commercial anhydrous 5% Rh/Al$_2$O$_3$ catalyst (with a precious metal content about 2.5 times higher than that of the present invention) in 150 ml of ethanol, were placed in a 250 ml autoclave.

After 6 hours at 20 atm (293.8 psi) and at 70° C., the conversion was less than 95% and the selectivity less than 96%.

The invention claimed is:

1. Process for preparing an Rh-based catalytic system heterogenized on an organic or mineral support, characterized in that:
   (a) a rhodium derivative with a valency state >0 is reduced in an ether or aromatic solvent and in the presence of a compound chosen from the group consisting of lipophilic tertiary amines, lipophilic tertiary amides and lipophilic quaternary ammonium salts, resulting in a mixture and
   (b) the mixture is adsorbed onto a suitable organic or mineral support;
   wherein the reduction is carried out by hydrogen transfer from a suitable hydrogen donor at a pressure of between 1 and 5 atm (14.69–73.45 psi) and at a temperature of between 15 and 40° C.

2. Process according to claim 1, wherein the rhodium derivative is a halide.

3. Process according to claim 2, wherein the ether or aromatic solvent is chosen from the group consisting of tetrahydrofuran, 1,2-dimethoxyethane, diglyme, toluene, mesitylene, isopropylbenzene and cumene.

4. Process according to claim 3, wherein the lipophilic tertiary amine is an amine of formula NTT'T", in which T, T' and T", which may be identical or different, are a linear or branched alkyl containing from 4 to 20 carbon atoms, a cycloalkyl containing from 5 to 10 carbon atoms or an alkylphenyl in which the alkyl contains from 1 to 20 carbon atoms.

5. Process according to claim 3, wherein the lipophilic tertiary amide is an amide X—CO—NX'X", in which X' and X", which may be identical or different, are a linear or branched alkyl containing from 4 to 20 carbon atoms, a cycloalkyl containing from 5 to 10 carbon atoms or an alkylphenyl in which the alkyl contains from 1 to 20 carbon atoms.

6. Process according to claim 3, wherein the lipophilic quaternary ammonium salt is a quaternary salt of formula [NY$^1$Y2Y$^3$Y$^4$]$^+$ Z$^-$ in which Y$^1$, Y$^2$, Y$^3$ and Y$^4$, which may be identical or different, are a linear or branched alkyl containing from 1 to 20 carbon atoms, a cycloalkyl containing from 5 to 10 carbon atoms or an alkylphenyl in which the alkyl contains from 1 to 20 carbon atoms, on condition that the total number of carbon atoms in the quaternary salt is at least 14; Z$^-$ is Br$^-$, Cl$^-$, OH$^-$ or HSO$_4$.

7. Process according to claim 4, wherein the tertiary amine trioctylamine or hexadecylamine.

8. Process according to claim 4, wherein the (amine or amide or ammonium salt)/rhodium salt molar ratio is between 2 and 5.

9. Process according to claim 8, wherein the mineral support is chosen from the group consisting of: Al$_2$O$_3$, pumice, hydrotalcite, C, SiO$_2$ zeolites, TiO$_2$ and ZrO$_2$.

10. Process according to claim 9, wherein the mineral support is a γ alumina.

11. Process according to claim 10, wherein the catalytic system is prepared in a single phase.

12. Process according to claim 1, wherein the ether or aromatic solvent is chosen from the group consisting of tetrahydrofuran, 1,2-dimethoxyethane, diglyme, toluene, mesitylene, isopropylbenzene and cumene.

13. Process according to claim 1, wherein the (amine or amide or ammonium salt)/rhodium salt molar ratio is between 2 and 5.

14. Process according to claim 1, wherein the mineral support is chosen from the group comprising: Al$_2$O$_3$, pumice, hydrotalcite, C, SiO$_2$ zeolites, TiO$_2$, and ZrO$_2$.

15. Process according to Claim 1, wherein the catalytic system is prepared in a single phase.

16. Process according to claim 1, wherein the reduction is carried out with hydrogen.

17. Process for hydrogenating the C═C double bond in α,β-unsaturated carbonyl compounds of general formula (I) according to the following reaction scheme:

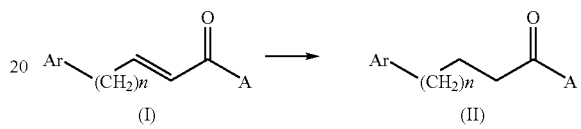

in which
A is hydrogen, linear or branched alkyl containing from 1 to 8 carbon atoms, cycloalkyl containing from 5 to 10 carbon atoms, COOR or CONRR' in which R and R', which may be identical or different, are hydrogen, linear or branched alkyl containing from 1 to 8 carbon atoms or cycloalkyl containing from 5 to 10 carbon atoms, or A has the meanings given below for Ar
n is 0, 1 or 2;
Ar is phenyl, naphthyl or a 5- to 7-membered heteroaryl containing 1 or 2 hetero atoms chosen from O, N and S, in which the said phenyl, naphthyl and heteroaryl may be substituted with one or more C$_1$–C$_2$ alkyl groups or one or more OH, OR, halogen, COOR or CONRR' groups, in which R and R', which may be identical or different, are hydrogen, benzyl, linear or branched alkyl containing from 1 to 8 carbon atoms or cycloalkyl containing from 5 to 10 carbon atoms, wherein
the hydrogenation is carried out by contacting α,β-unsaturated carbonyl compounds with an Rh-based catalytic system prepared according to claim 4.

18. Process according to claim 17, wherein the hydrogenation is carried out at a temperature of between 0° and 100° C.

19. Process according to claim 18, wherein the hydrogenation is carried out at a temperature of between 20° and 80° C.

20. Process according to claim 19, wherein the hydrogenation is carried out at a pressure of between 1 (14.69 psi) and 20 atm (293.8 psi).

21. Process according to claim 20, wherein the hydrogenation is carried out in the presence of a solvent of medium or low polarity chosen from the group comprising linear or branched aliphatic hydrocarbons containing from 6 to 12 carbon atoms; cyclic hydrocarbons containing from 6 to 10 carbon atoms; aromatic hydrocarbons: aliphatic esters; aliphatic ethers and chlorinated aliphatic solvents.

22. Process according to claim 21, wherein the solvent of medium or low polarity is chosen from the group comprising toluene, xylene, mesitylene, isopropylbenzene, cumene, ethyl acetate, isopropyl acetate, butyl acetate, tetrahydrofuran and mesitylene chloride.

23. Process according to claim 22, wherein in the compound of general formula (I), Ar is (6'-methoxy-2'-naphthyl) or (2',3'-dimethoxyphenyl), n=0 and A is methyl, COOH, COOO($C_1$–$C_4$)alkyl or COO-benzyl.

24. Process according to claim 17, wherein the hydrogenation is carried out at a pressure of between 1 (14.69 psi) and 20 aim (293.8 psi).

25. Process according to claim 17, wherein the hydrogenation is carried out in the presence of a solvent of medium or low polarity chosen from the group comprising linear or branched aliphatic hydrocarbons containing from 6 to 12 carbon atoms; cyclic hydrocarbons containing from to 10 carbon atoms; aromatic hydrocarbons: aliphatic esters; aliphatic ethers and chlorinated aliphatic solvents.

26. Process according to claim 17, characterized that, wherein in the compound of general formula (I), Ar is (6'-methoxy-2'-naphthyl) or (2',3'-dimethoxyphenyl), n=0 and A is methyl, COOH, COOO(C1–C4)alkyl or COO-benzyl.

* * * * *